(12) United States Patent
Krueger et al.

(10) Patent No.: US 12,663,637 B2
(45) Date of Patent: Jun. 23, 2026

(54) FIBER OPTIC LENS CLEANING BY GAS FLOW AND/OR VIBRATIONS

(71) Applicant: GE Precision Healthcare LLC, Waukesha, WI (US)

(72) Inventors: Paul Krueger, Pewaukee, WI (US); Jiaqi Li, Pewaukee, WI (US); Robert Nevermann, Whitefish Bay, WI (US); Dixin Mi, Hartland, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 281 days.

(21) Appl. No.: 18/431,842

(22) Filed: Feb. 2, 2024

(65) Prior Publication Data

US 2025/0251589 A1 Aug. 7, 2025

(51) Int. Cl.
| | |
|---|---|
| *A61B 5/00* | (2006.01) |
| *A61B 5/055* | (2006.01) |
| *A61B 90/00* | (2016.01) |
| *B08B 5/02* | (2006.01) |
| *B08B 7/02* | (2006.01) |

(Continued)

(52) U.S. Cl.
CPC ........ *G02B 27/0006* (2013.01); *A61B 5/0033* (2013.01); *G01R 33/283* (2013.01); *G01R 33/34* (2013.01); *G01R 33/3692* (2013.01); *A61B 5/0046* (2013.01); *A61B 5/055* (2013.01); *A61B 5/704* (2013.01); *A61B 2090/374* (2016.02);

(Continued)

(58) Field of Classification Search
CPC ..... A61B 5/0033; A61B 5/0046; A61B 5/055;

A61B 5/704; A61B 2090/374; B08B 5/02; B08B 7/02; B08B 2240/02; G01R 33/28; G01R 33/283; G01R 33/34; G01R 33/3692; G02B 27/0006

See application file for complete search history.

(56) References Cited

U.S. PATENT DOCUMENTS

| | | | |
|---|---|---|---|
| 7,356,236 B1 | 4/2008 | Huang et al. | |
| 8,899,761 B2 | 12/2014 | Tonar et al. | |

(Continued)

FOREIGN PATENT DOCUMENTS

| | | | | |
|---|---|---|---|---|
| DE | 102021200756 A1 | * | 7/2022 | ......... G01R 33/3692 |
| WO | 2008072822 A1 | | 6/2008 | |

OTHER PUBLICATIONS

English translation of DE 10-2021-200756 A1 of Sukkau (retreived from https://worldwide.espacenet.com/ on Jan. 3, 2026; original document published Jul. 28, 2022).*

(Continued)

*Primary Examiner* — Ryan S Dunning
(74) *Attorney, Agent, or Firm* — McCoy Russell LLP

(57) ABSTRACT

Methods and systems are provided for an automatic lens cleaning system incorporated into a system. The system includes an imaging device, a reversibly coupled table configured to reversibly couple to the imaging device, a communication interface including a first lens of the imaging device and a second lens of the reversibly coupled table, and the automatic lens cleaning system. The automatic lens cleaning system includes a bellow positioned at a coupling interface between the imaging device and the reversibly coupled table, and at least one nozzle fluidly coupled to the bellow and configured to direct a flow of gas towards at least one of the first lens or the second lens.

19 Claims, 10 Drawing Sheets

(51) Int. Cl.
    *G01R 33/28*          (2006.01)
    *G01R 33/34*          (2006.01)
    *G01R 33/36*          (2006.01)
    *G02B 27/00*          (2006.01)

(52) U.S. Cl.
    CPC . *B08B 5/02* (2013.01); *B08B 7/02* (2013.01);
               *B08B 2240/02* (2013.01); *G01R 33/28*
                               (2013.01)

(56)                References Cited

U.S. PATENT DOCUMENTS 9,083,864 B2    7/2015   Reed
9,354,401 B2    5/2016   Leigh et al.

OTHER PUBLICATIONS

"Canon EOS—Integrated Cleaning System," YouTube Website, Available Online at https://www.youtube.com/watch?v=x939m5bGhFM, May 21, 2009, 2 pages.
Schmieding, D. et al., "System and Methods for Control of Motion-Assisted Table," U.S. Appl. No. 18/471,173, filed Sep. 20, 2023, 39 pages.

* cited by examiner

FIBER OPTIC LENS CLEANING BY GAS FLOW AND/OR VIBRATIONS

TECHNICAL FIELD

Embodiments of the subject matter disclosed herein relate to systems and methods for cleaning fiber optic lenses of an imaging system.

BACKGROUND

In some examples an imaging system may include an imaging device reversibly coupled to a patient table. Fiber optics may communicatively couple the imaging device to the patient table. Fiber optics may reduce a cost and size compared to using electrical conductors for communication. However, when uncoupled, an exposed surface of a lens of the fiber optics may become dusty or covered with other contaminants. Without cleaning, the dust may interfere with data transmission between the imaging device and the patient table.

BRIEF DESCRIPTION

In one embodiment, the system comprises an imaging device, a reversibly coupled table, configured to reversibly couple to the imaging device, a communication interface comprising a first lens of the imaging device and second lens of the reversibly coupled table, and an automatic lens cleaning assembly comprising a bellow positioned at a coupling interface between the medical imaging system and the reversibly coupled table and at least one nozzle fluidly coupled to the bellows, where at least one nozzle is configured to direct a flow of gas towards at least one of the first lens or the second lens.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, herein below.

DETAILED DESCRIPTION

Figure 1:
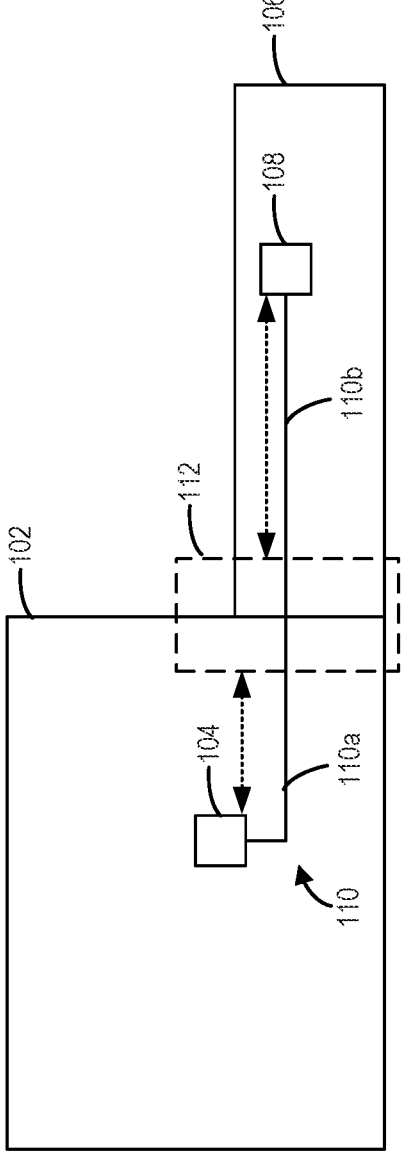
FIG. 1 shows a diagram of an imaging system including a reversibly coupled table and an automatic lens cleaning system in a coupled state.
Figure 1:
Figure 2:
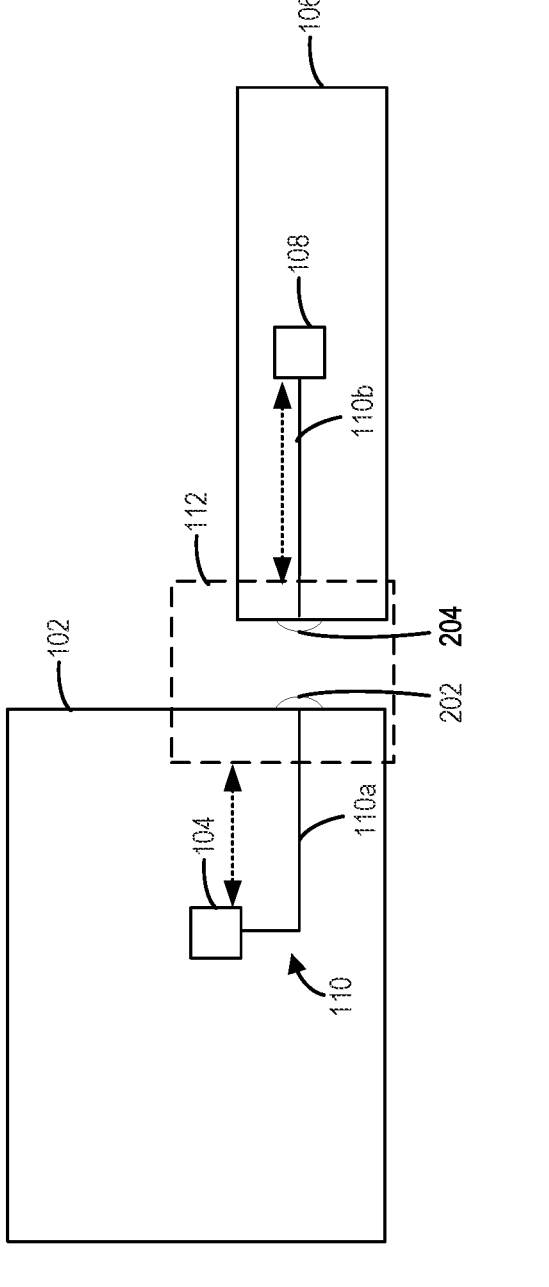
FIG. 2 shows a diagram of the imaging system of FIG. 1 in a decoupled state.
Figure 2:
Figure 3:
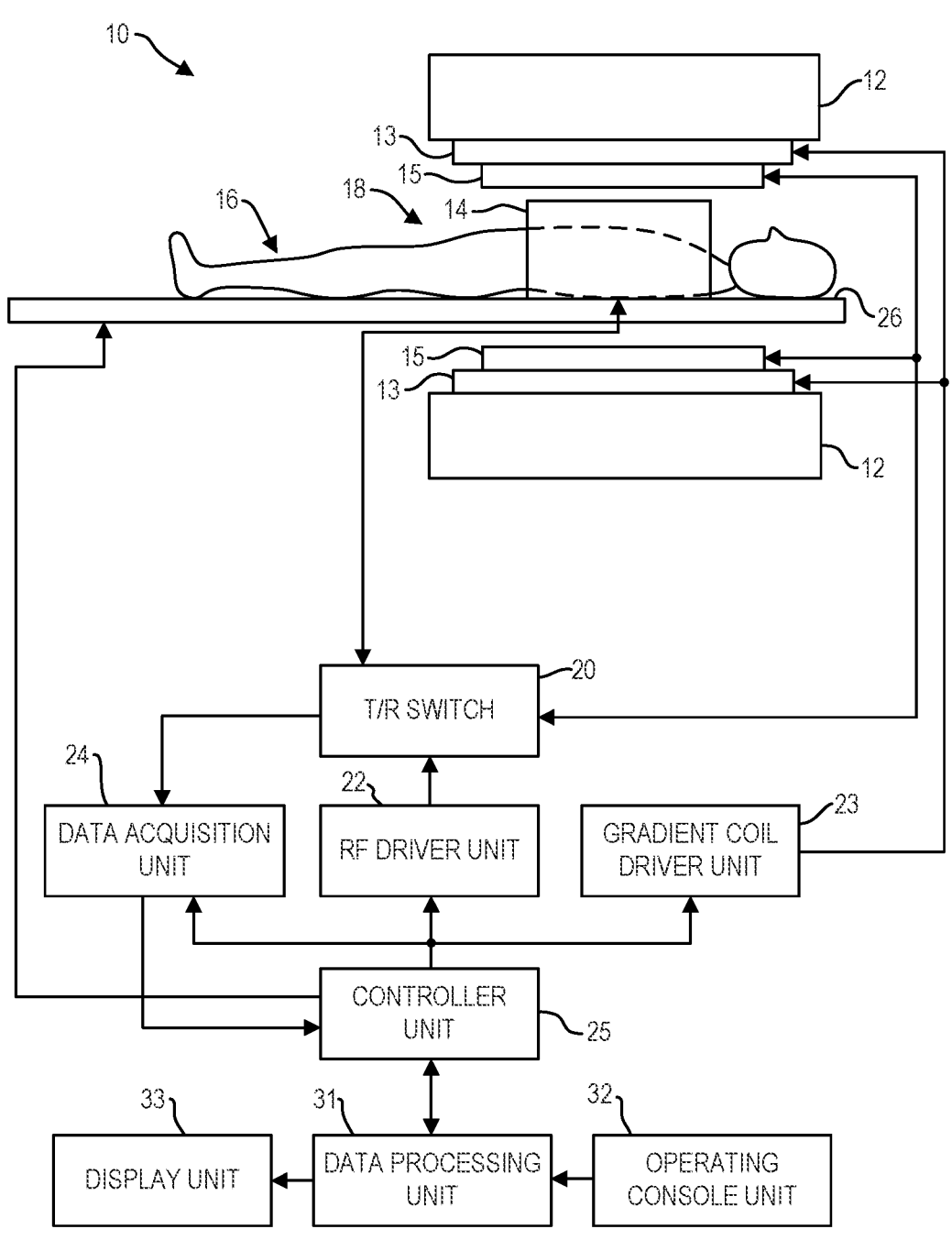
FIG. 3 shows a diagram of a magnetic resonance imaging apparatus.
Figure 4:
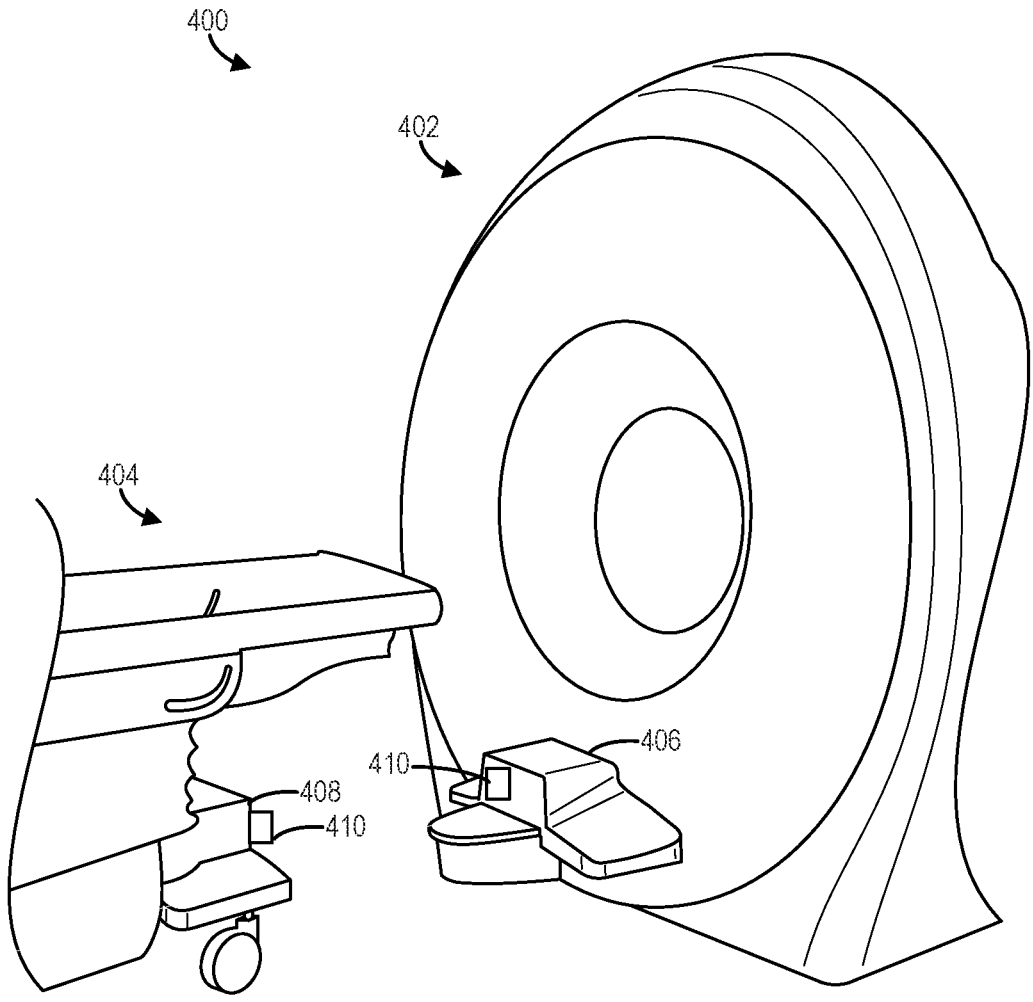
FIG. 4 shows an example of a magnetic resonance imaging apparatus including a reversibly coupled table and an automatic lens cleaning system.

The following description relates to systems and methods for cleaning fiber optic lenses of a docking system wherein a first component is reversibly coupled to a second component and the two components are communicatively coupled by a fiber optic cable. In one example, the docking system is an imaging system including a detachably coupled patient table. FIG. 1 shows an example of an imaging system including a reversibly coupled patient table in a coupled state and FIG. 2 shows the imaging system in a decoupled state. As one example, the imaging system may be a magnetic resonance system as shown in FIG. 3. An example of a magnetic resonance system including a reversibly coupled patient table is shown in FIG. 4. Herein, reversibly coupled refers to the ability to couple and decouple repeatedly without degradation of the components and without demanding any disassembly or reassembly. For example, the reversibly coupled patient table may be configured to be routinely communicatively coupled to and decoupled from an imaging device without being destructive to the patient table or imaging device and without demanding any disassembly or subsequent re-assembly of the imaging system. In this way, the reversibly coupled patient table may be used by a clinician to retrieve a patient from a location outside the imaging room and transport them to the imaging device, couple the patient table to the imaging device, and proceed with an imaging procedure without performing an additional patient transfer. In some examples, one or more fiber optic cables may be used to transfer data between the imaging device and the reversibly coupled patient table. The one or more fiber optic cables may be divided into an imaging device portion and a table portion reversibly coupled together at a communication interface of the imaging system and the reversibly coupled patient table, comprising a first lens positioned on an outer surface of the imaging device and a second lens positioned on an outer surface of the reversibly coupled patient table.

When in a decoupled state, a lens of the imaging device portion and a lens of the table portion (e.g., the lenses) may accumulate dust which may degrade the fiber optic and/or a communication signal carried by the fiber optic. A clinician may clean each of the lens of the imaging device portion and the lens of the table before docking, but such actions would then be subject to human memory/error and would take additional time. An automatic lens cleaning system as shown in FIG. 1 automatically cleans the lenses each time the reversibly coupled patient table is coupled to the imaging device. In this way, cleaning is performed without counting on a clinician's thoroughness and the clinician's time is saved. As a further example, cleaning of the lens may demand attention from a specialized service technician and an automatic system, such as the automatic lens cleaning system saves the money and time demanded for a specialized service technician.

Figure 5:
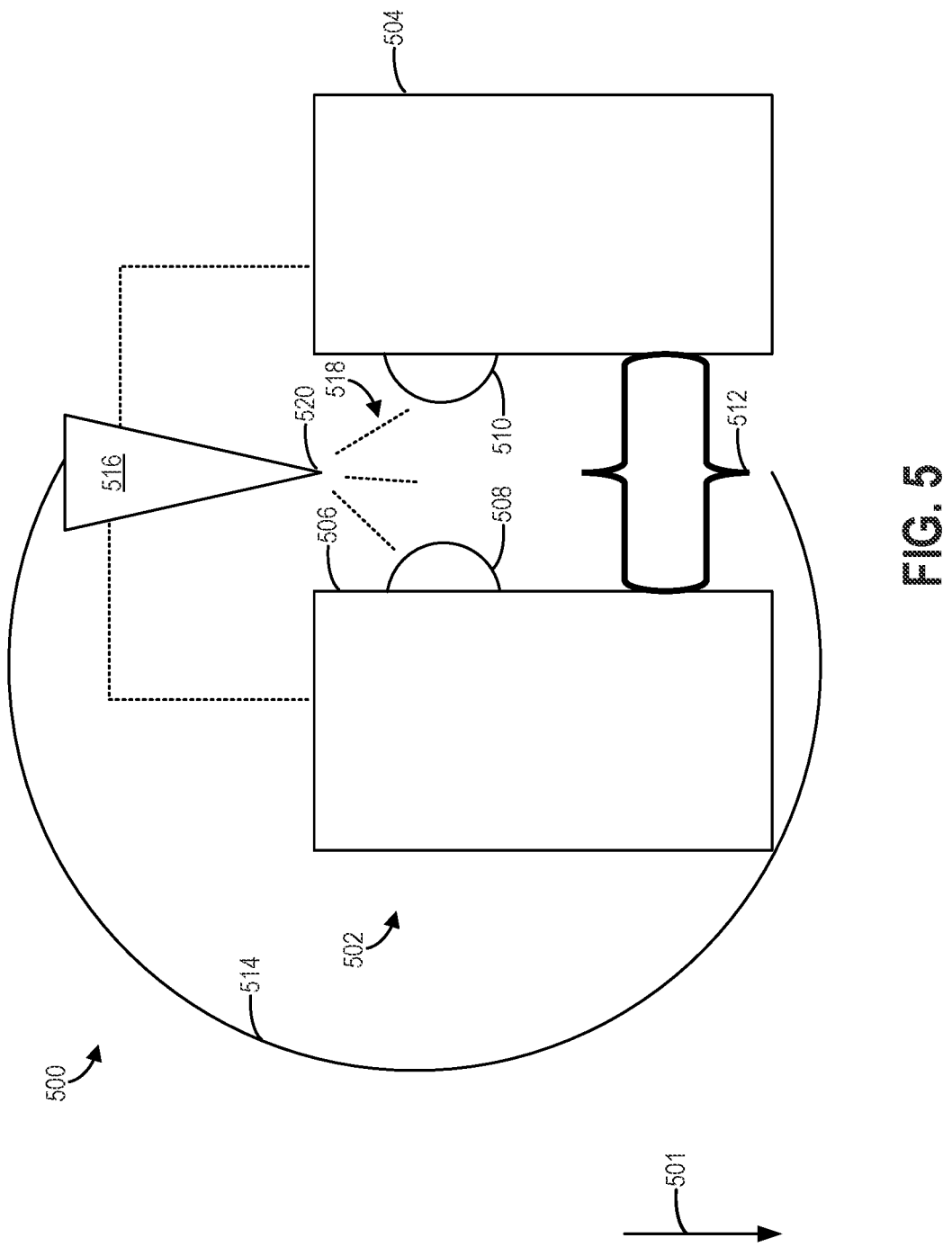
FIG. 5 shows a first embodiment of an automatic lens cleaning system including a bellows and a nozzle.
Figure 6:
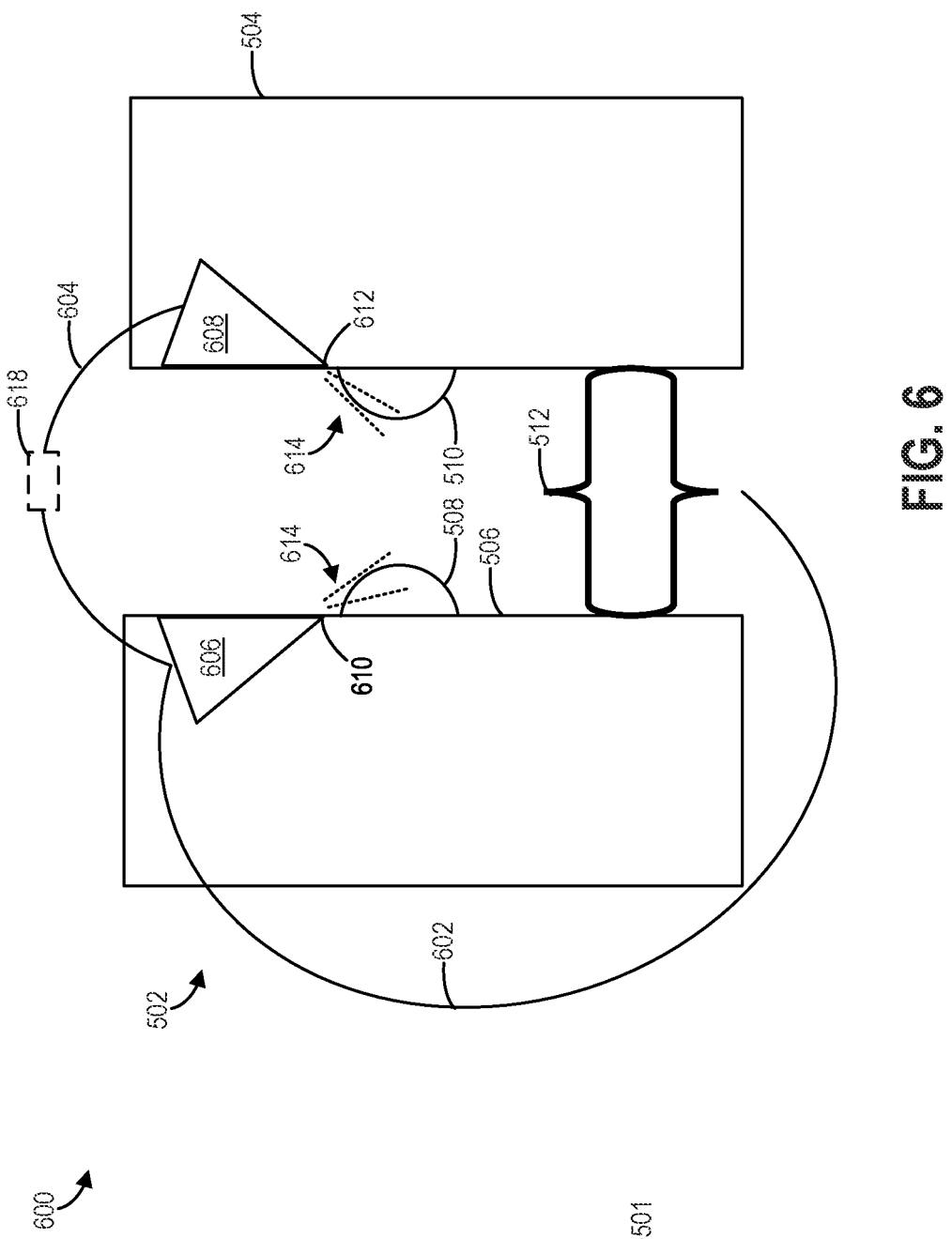
FIG. 6 shows a second embodiment of an automatic lens cleaning system including a bellows and embedded nozzles.
Figure 7:
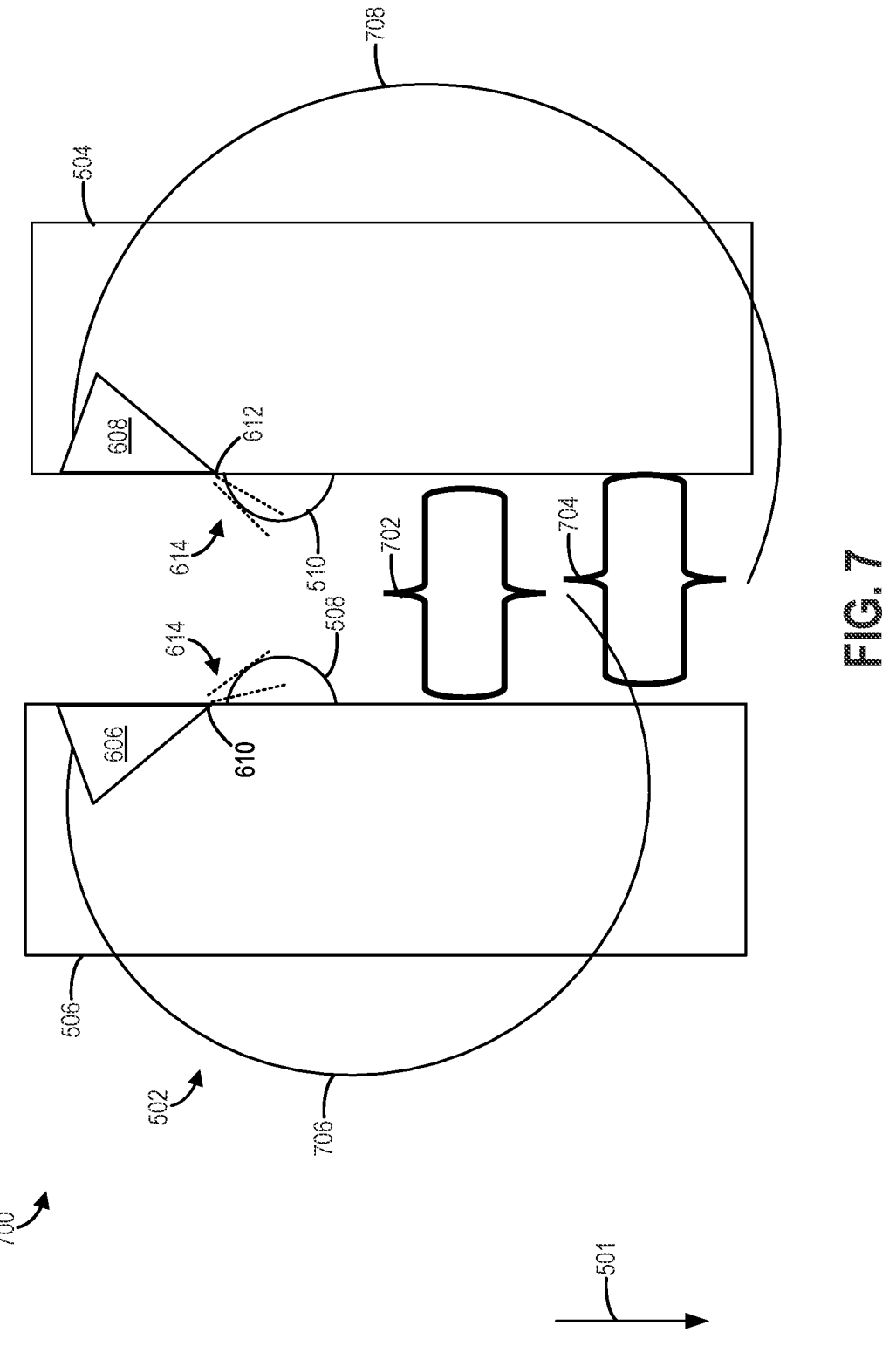
FIG. 7 shows a third embodiment of an automatic lens cleaning system including dual bellows and embedded nozzles.
Figure 8:
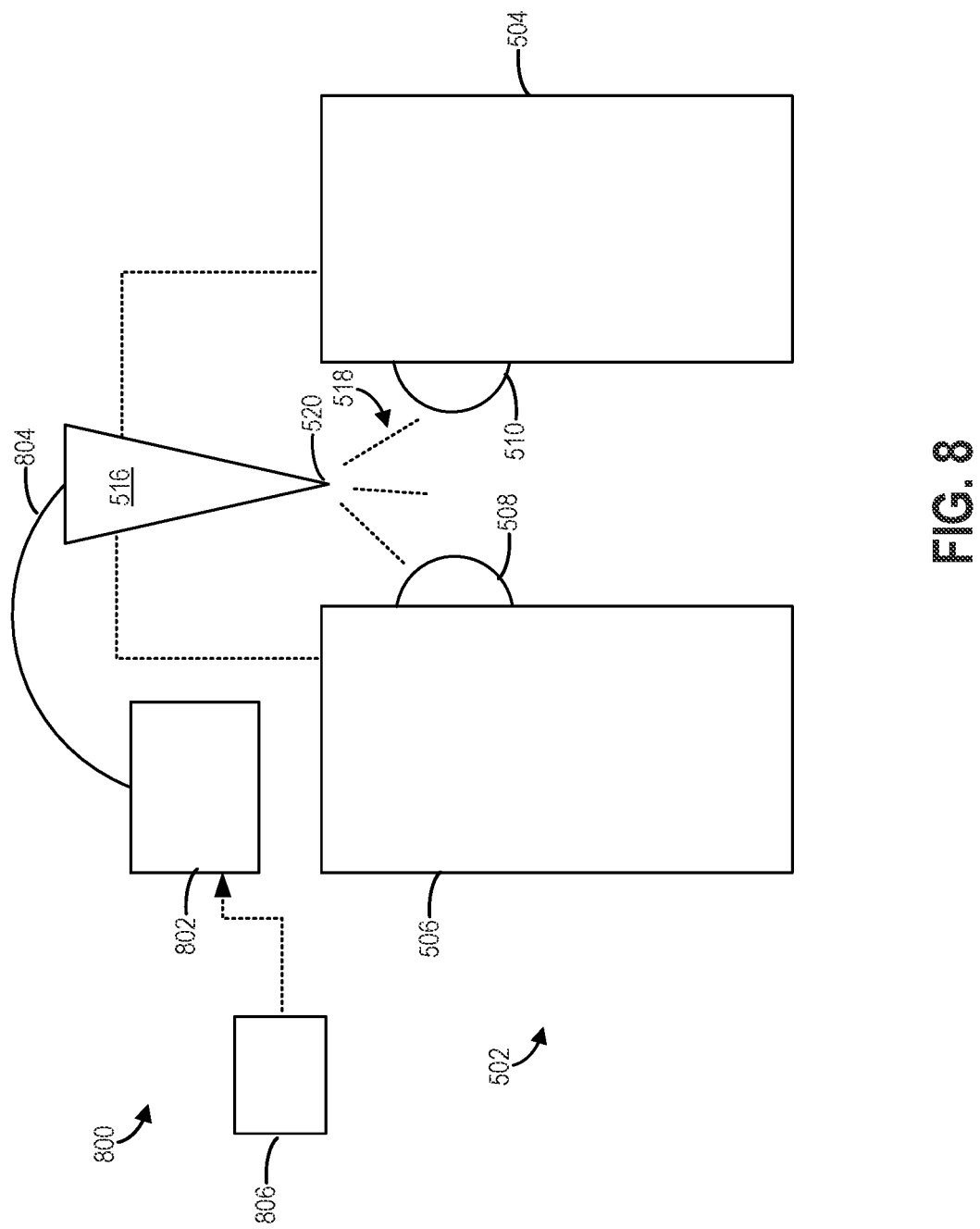
FIG. 8 shows a fourth embodiment of an automatic lens cleaning system including a nozzle and an alternate gas source.
Figure 9:
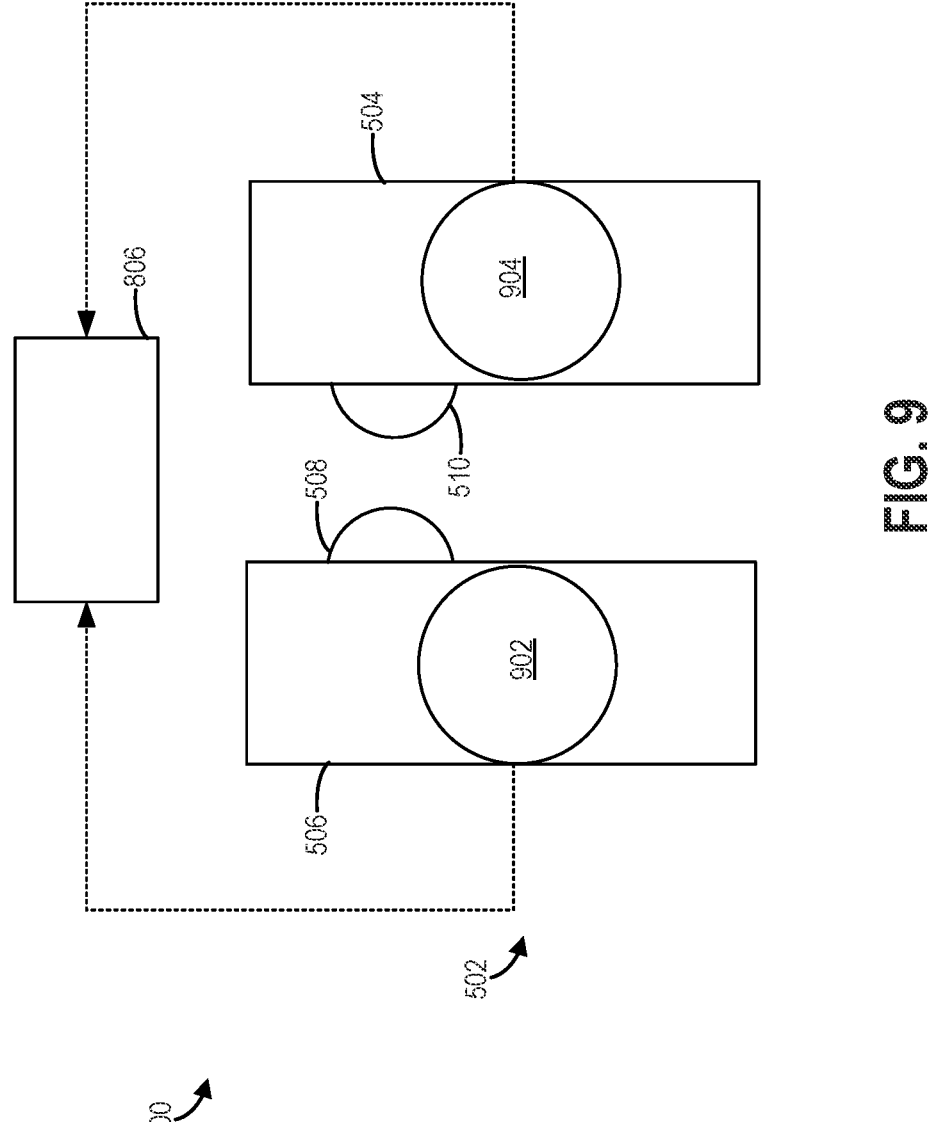
FIG. 9 shows a fifth embodiment of an automatic lens system including vibratory cleaners.
Figure 10:
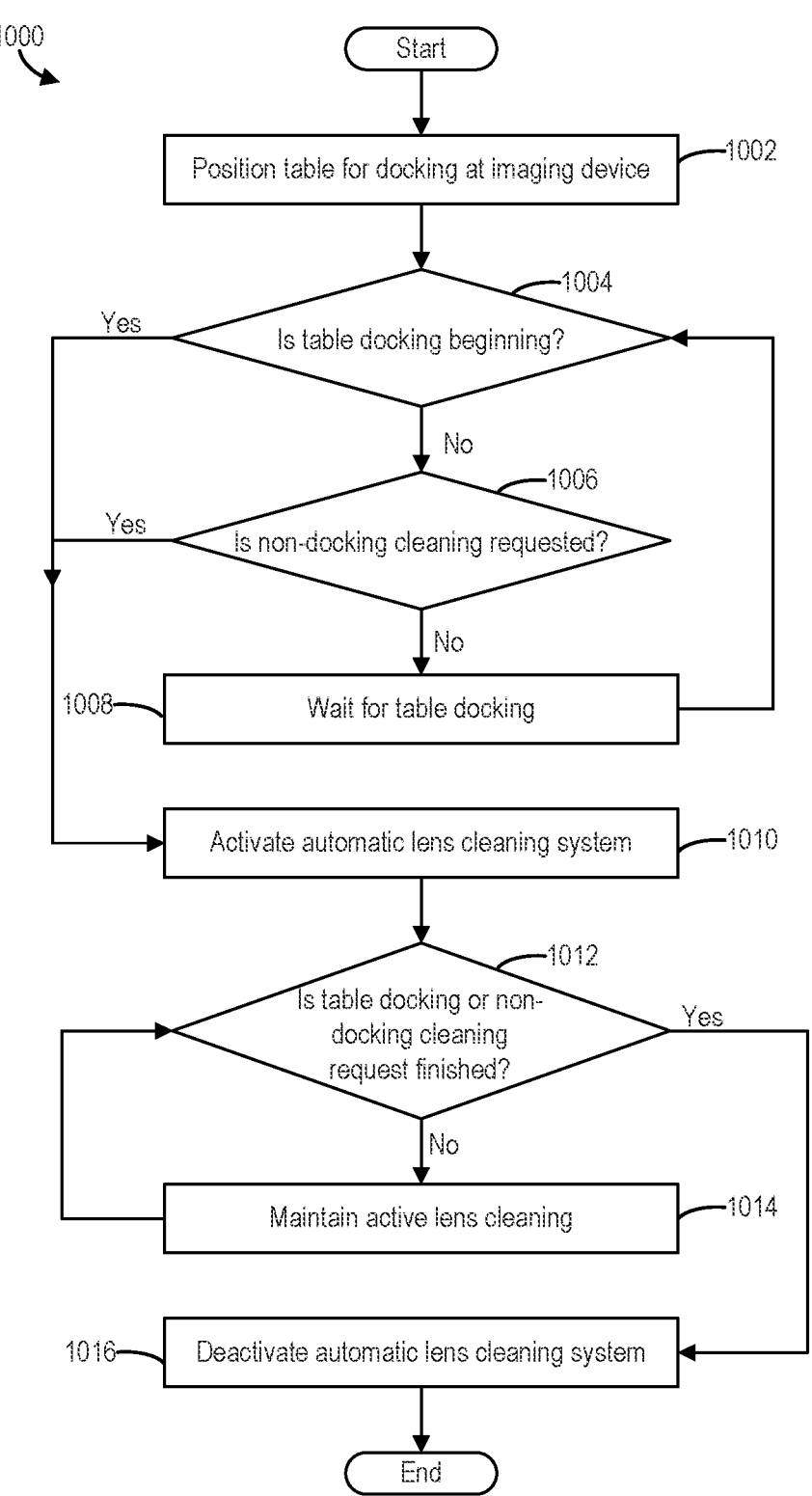
FIG. 10 shows a flowchart of an example of a method for operating an automatic lens cleaning system.

In one embodiment, the automatic lens cleaning system may be a passive system using one or more bellows coupled to a nozzle as shown in FIGS. 5-7. The bellows may be automatically compressed between surfaces of the imaging device and reversibly coupled patient table when coupled, thereby directing gas flow to surfaces of the lenses. In alternate embodiments, the automatic lens cleaning system may be an active system. For example, a gas compressor or similar system may be used to provide a flow of gas towards the lenses as shown in FIG. 8. As an alternate example, vibratory motors may be used to shake dust off of the lenses as shown in FIG. 9. In examples where the automatic lens cleaning system is an active system, a method for controlling the automatic lens cleaning system is shown in FIG. 10.

Turning now to FIG. 1, an imaging system 100 is shown including an imaging device 102 and a reversibly coupled table 106 in a coupled state. The imaging system 100 may be configured to probe a patient with electromagnetic or acoustic waves and receive the returned electromagnetic or acoustic waves to form a medical image of the patient. As one example, imaging device 102 may be a magnetic resonance device and the imaging system 100 may be a magnetic resonance imaging apparatus (MRI) as described further below with respect to FIGS. 3 and 4.

Imaging device 102 may include a device controller 104 and reversibly coupled table 106 may include a table controller 108. When in the coupled state, the imaging system 100 may be ready to capture images of the patient. Capturing images of the patient may include communication of instructions and imaging information between device controller 104 and table controller 108. Data communication may occur via a fiber optic cable 110. Fiber optic cable 110 may include a device portion 110a physically coupled to imaging device 102 and a table portion 110b physically coupled to reversibly coupled table 106. Device portion 110a may be coupled at a first end to device controller 104 and at a second end to table portion 110b. Table portion 110b may be coupled at a first end to table controller 108 and at a second end to device portion 110a. When imaging system 100 is in the coupled state device portion 110a may be coupled to table portion 110b. In the coupled state, lenses of fiber optic cable 110 may be not be exposed to contaminants present in an atmosphere surrounding imaging system 100.

When in a decoupled state, as shown in FIG. 2, device portion 110a of fiber optic cable 110 may not be coupled to table portion 110b. Further, at least a portion of imaging device 102 may be spaced away from reversibly coupled table 106. In this way, a device lens 202 positioned at the second end of device portion 110a and a table lens 204 positioned at the second of table portion 110b may each be exposed to the atmosphere surround imaging system 100. Device lens 202 and table lens 204 may comprise a communication interface of imaging system 100. The atmosphere may include dust particles and other contaminants which may collect on an outer surface of device lens 202 and table lens 204. The dust and other contaminants may scatter the light used to carry data on fiber optic cable 110 and may further scratch and/or degrade a surface of device lens 202 and table lens 204. For this reason, an automatic lens cleaning system 112 may be included in imaging system 100.

The automatic lens cleaning system 112 may be configured to automatically remove dust and other contaminants from the exposed outer surface of device lens 202 and table lens 204 immediately prior to imaging system 100 transitioning from the decoupled state to the coupled state. As described further below, automatic lens cleaning system 112 may be included in imaging device 102 and/or in reversibly coupled table 106. In some examples automatic lens cleaning system 112 may be passive and may not be coupled to device controller 104 or to table controller 108. In alternate examples, automatic lens cleaning system 112 may be an active system and may be communicatively coupled to device controller 104 or table controller 108. Embodiments of automatic lens cleaning system 112 are discussed further below with reference to FIGS. 5-9.

In exemplary embodiment, the imaging system 100 may be a magnetic resonance imaging apparatus as shown in FIG. 3. FIG. 3 illustrates a magnetic resonance imaging (MRI) apparatus 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25. In some examples, the table 26 may be reversibly coupled table similar to reversibly coupled table 106 of FIGS. 1-2.

The controller unit 25 includes a computer and a recording medium on which a program to be executed by the computer is recorded. In some examples, controller unit 25 may include a controller of the table 26. The program when executed by the computer causes various parts of the apparatus to carry out operations corresponding to pre-determined scanning. Additionally, the program may include instructions related to actuation of an automatic lens cleaning system, such as automatic lens cleaning system 112 of FIGS. 1-2. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

Turning now to FIG. 4, an example of an MRI apparatus 400 is shown which may be an embodiment of MRI apparatus 10 of FIG. 3. MRI apparatus may include an imaging device 402 and a reversibly coupled table 404. Both imaging device 402 and reversibly coupled table 404 may include similar components to MRI apparatus 10 as discussed above with respect to FIG. 3. As one example, reversibly coupled table 404 may include a docking device 408 configured to couple to a dock 406 of imaging device 402. In one embodiment docking device 408 and dock 406 may be positioned at a lower portion (e.g., closer to a floor on which MRI apparatus 400 rests) of reversibly coupled table 404 and imaging device 402 respectively. Further, lenses of a fiber optic cable similar to fiber optic cable 110 of FIGS. 1-2 may be included in docking device 408 and dock 406. Additionally, an automatic lens cleaning system 410 may also be included in the MRI apparatus 400. Automatic lens cleaning system 410 may be included in docking device 408 and/or dock 406. Embodiments of an automatic lens cleaning system, such as automatic lens cleaning system 410 are discussed further below with respect to FIGS. 5-10.

When a lens of a fiber optic system is exposed to a dusty environment, such as when a reversibly coupled table and an imaging device are in a decoupled state, dust and/or other particles may accumulate on the lens. An operator may be held responsible for cleaning the lens of the accumulated dust and/or other particles before transitioning to the coupled state, but it is possible for a human operator to forget the step. Further, an operator may not be trained to clean a fiber optic lens and cleaning the fiber optic lens may demand attention of a specially trained technician. A system to automatically clean the fiber optic lens may avoid the demand for additional human labor hours and may clean the lens in a consistent and reliable fashion before transitioning to the coupled state from the decoupled state. In this way, the lenses are not scratched or degraded by the dust and reliable communication between the reversibly coupled table and the imaging device are maintained.

FIGS. 5-9 describe embodiments of an automatic lens cleaning system. A docking system may include one or more of the embodiments described herein. Turning now to FIG. 5, a first embodiment of an automatic lens cleaning system 500 coupled to a docking system 502 in a decoupled state. An arrow 501 shows a direction of gravity. Docking system 502 may include a first component 506 and a second component 504. In an exemplary embodiment, first component 506 may be included in an imaging device of an imaging system such as imaging device 102 of imaging system 100 and second component 504 may be included in a reversibly coupled table such as reversibly coupled table 106. Further, first component 506 and second component 504 may be included in an MRI device and a reversibly coupled table of an MRI apparatus, such as MRI apparatus 400 of FIG. 4. Further, first component 506 may be a docking device and second component 504 may be a dock, such as docking device 408 and dock 406 of FIG. 4. A first lens 508 of a fiber optic cable may be protrude from first component 506 and a second lens 510 of the fiber optic cable may protrude from second component 504. First lens 508 and second lens 510 may comprise a communication interface and may be adapted to be at a fixed communication distance from each other when docking system is in a coupled state. At the fixed communication distance, information may be transferred between first component 506 and second component 504 through first lens 508 and second lens 510 over a fiber optic line. As one example, the communication interface may be a contactless interface and the fixed distance may be greater than zero. When the docking system is in the coupled state, first lens 508 may closer to second lens 510 than when the docking system is in the decoupled state, but first lens 508 may still be spaced apart from second lens 510.

Automatic lens cleaning system 500 may include a bellows 512, a hose 514, and a nozzle 516. Bellows 512 may be positioned between first component 506 and second component 504. In some embodiments, bellows 512 may be physically coupled to first component 506. In alternate embodiment, bellow 512 may be physically coupled to second component 504. Bellows 512 may be fluidly coupled to the nozzle 516 via the hose 514. In some examples, automatic lens cleaning system 500 may include a plurality of bellows, each positioned between first component 506 and second component 504. In some examples, each of the plurality of bellows may be fluidly coupled to each other via one or more hoses or nozzles. In some examples a single bellows 512 may act as a manifold, fluidly coupled via one or more hoses to one or more nozzles. In further examples, docking system 502 may include a plurality of automatic lens cleaning systems, each including a fluidly separate bellows and nozzle.

When docking system 502 is transitioned from a decoupled state to a coupled state, first component 506 may be moved physically closer to second component 504 and bellows 512 may be compressed between outer surfaces of first component 506 and second component 504, thereby forcing gas flow through hose 514 and out of an opening 520 of nozzle 516. Bellows 512 may be configured to be filled and expel gas of an ambient atmosphere of docking system 502. For example, the gas flow may be ambient air. In alternate examples, docking system 502 may be in an atmosphere comprising a different mixture of gasses. In some examples, nozzle 516 may be physically coupled to the first component or the second component. In some examples, hose 514 may be rigid enough to support nozzle 516 above first lens 508 and second lens 510 with respect to a direction of gravity. In some examples, bellows 512 may be fluidly coupled to more than one nozzle. In some examples nozzle 516 may positioned above first lens 508 and above second lens 510 with respect to gravity, a direction of gravity indicated by arrow 501. In some examples, opening 520 may be pointed directly downward with respect to gravity and not angled toward first lens 508 and/or second lens 510. In alternate examples, opening 520 may be angled towards first lens 508 and/or second lens 510. In further examples, automatic lens cleaning system 500 may include a plurality of nozzles and each nozzle may be angled differently. Gas flow, represented by lines 518, may flow from opening 510 when bellows 512 is compressed and pass over surfaces of first lens 508 and second lens 510, thereby removing dust or other contaminants from an outer surface of first lens 508 and second lens 510. As one example, positioning nozzle 516 above first lens 508 and second lens 510, with respect to gravity, may allow gravity to help move dust and contaminants away from first lens 508 and second lens 510.

Turning now to FIG. 6, a second embodiment 600 of an automatic lens cleaning system is shown coupled to docking system 502. Second embodiment 600 may include some of the same components as automatic lens cleaning system 500. Such components are labeled the same and are not reintroduced.

Second embodiment 600 may include a first embedded nozzle 606 embedded into first component 506 and a second embedded nozzle 608 embedded into second component 504. In some embodiments, first embedded nozzle 606 and second embedded nozzle 608 may each be integrally formed with first component 506 and second component 504 respectively. An opening 610 of first embedded nozzle 606 may be positioned above first lens 508 with respect to the direction of gravity. Similarly, an opening 612 of second embedded nozzle 608 may positioned above second lens 510 with respect to the direction of gravity. In some examples, first component 506 and second component 504 may each include a plurality of embedded nozzles. The plurality of embedded nozzles may be fluidly coupled to one or more bellows. Gas flow represented by lines 614 may be directed from opening 610 and opening 612 when bellows 512 is compressed as first component 506 and second component 504 are being coupled.

A first hose 602 may fluidly couple bellows 512 to first embedded nozzle 606. A second hose 604 may fluidly couple first embedded nozzle 606 to second embedded nozzle 608. In such examples, bellows 512 may be physically coupled to first component 506. In alternate examples, first hose 602 may fluidly couple bellows 512 to second embedded nozzle 608 and bellows 512 may be physically coupled to second component 504. In some examples, first hose 602 and second hose 604 may be at least partially embedded in first component 506 and/or second component 504. In some examples, second hose 604 may include a coupler 618. Coupler 618 may be configured to reversibly separate second hose 604 into a portion coupled to first embedded nozzle 606 and a portion coupled to second embedded nozzle 608. In this way, a distance between first component 506 and second component 504 in a decoupled state may not be limited by a length of second hose 604. Additionally, a length of second hose 604 and a position of coupler 618 may be adapted to couple the two portions of second hose 604 before bellows 512 is compressed when docking system 502 transitions from the decoupled state to the coupled state.

Turning now to FIG. 7, a third embodiment 700 of an automatic lens cleaning system is shown coupled to docking system 502. Third embodiment 700 may include some of the same components as first embodiment of automatic lens cleaning system 500 and second embodiment 600. Such components are labeled the same and are not reintroduced.

Third embodiment 700 may include a first bellows 702 fluidly coupled to first embedded nozzle via a first hose 706. First bellows 702 may be physically coupled to first component 506. Third embodiment 700 may further include a second bellows 704 fluidly coupled to second embedded nozzle 608. Second bellows 704 may be physically coupled to second component 504. In some embodiments, first hose 706 may be at least partially embedded in first component 506 and second air hose 708 may be at least partially embedded in second component 504. In this way, a distance between first component 506 and second component 504 may not be limited when in a decoupled state and both first bellows 702 and second bellows 704 may be compressed when transitioning from the decoupled state to the coupled state. In some examples, first bellows 702 and/or second bellow 704 may include a plurality of bellows forming a manifold or coupled to one or more nozzles as described above with respect to FIGS. 5 and 6. First bellows 702 is shown above second bellows 704 for clarity, however, first bellows 702 may be positioned even with second bellows 704 with respect to a direction of gravity or other relative positions of first bellow 702 and second bellows 704 are considered.

Turning now to FIG. 8, a fourth embodiment 800 of an automatic lens cleaning system is shown coupled to docking system 502. Fourth embodiment 800 may include some of the same components as automatic lens cleaning system 500. Such components are labeled the same and are not reintroduced.

Fourth embodiment 800 may include an alternate gas source 802 fluidly coupled to nozzle 512 via hose 804. Alternate gas source 802 may be used in place of or in addition to bellows such as bellows 512. Further, fourth embodiment 800 may additionally or alternatively include alternate gas source 802 coupled to an embedded nozzle such as first embedded nozzle 606 and second embedded nozzle 608. In some examples, alternate gas source 802 may be fluidly coupled to nozzle 516 or embedded nozzles via hose 804. In some examples, fourth embodiment 800 may include a plurality of nozzles coupled to alternate gas source 802 by a plurality of hoses. In some examples, alternate gas source 802 may be a plurality of a sources coupled to one or more nozzles. Alternate gas source 802 may be physically coupled to first component 506 and/or second component 504. Additionally or alternatively, alternate gas source 802 may be embedded or integrally formed with first component 506 or second component 504. Alternate gas source 802 may be configured to direct a flow of gas into nozzle 516 or a plurality of nozzles as described above. For example, alternate gas source 802 may include one or more of a gas compressor, compressed gas tank, or patient blower, among others. A patient blower may include a wall mounted fan fluidly coupled to flexible ductwork adapted to flow air towards a patient positioned on the docking system 502. Additional ductwork may be used to direct gasses into nozzle 516 or a plurality of nozzles.

Alternate gas source 802 may demand an external actuation signal to provide gas flow, as opposed to the bellows which are automatically mechanically activated when compressed between first component 506 and second component 504. For this reason, alternate gas source 802 may be communicatively coupled to a controller 806. Controller 806 may be a controller of first component 506 or second component 504. In examples including a plurality of alternate gas sources, controller 806 may include a controller coupled of first component 506 and a controller of second component 504 each coupled one of the plurality of air sources. In some examples, controller 806 may be similar to device controller 104 and/or table controller 108 as described above with respect to FIGS. 1-2. As one example, controller 806 may be a controller of an MRI apparatus, such as controller 25 of FIG. 3. Controller 806 may include instructions stored on non-volatile memory of the controller to actuate alternate gas source 802 to flow gas through nozzle 516. Further examples of instructions are given in the method described below with respect to FIG. 10. For example, when alternate gas source 802 is a gas compressor, controller 806 may include instructions to energize and de-energize the gas compressor. As an alternate example, when alternate gas source 802 is a compressed gas tank, controller 806 may include instructions to open and close a valve positioned in a flow path between the compressed gas tank and the nozzle.

Turning now to FIG. 9, a fifth embodiment 900 of an automatic lens cleaning system is shown coupled to docking system 502. Fifth embodiment 900 may include some of the same components as automatic lens cleaning system 500 and fourth embodiment 800. Such components are labeled the same and are not reintroduced.

Fifth embodiment 900 may include a first vibration motor 902, physically coupled to first component 506 and a second vibration motor 904 physically coupled to second component 504. In some examples, first vibration motor 902 and/or second vibration motor may be positioned on an external surface of first component 506 and second component 504 respectively. In alternate examples, first vibration motor 902 and second vibration motor 904 may be embedded within first component 506 and second component 504 respectively. First vibration motor 902 and second vibration motor 904 may each, when energized, vibrate and the vibrations may be transmitted through the first component 506 and second component 504 to first lens 508 and second lens 510 respectively. For example, first vibration motor 902 and second vibration motor 904 may include a motor configured to rotate a counterweight at a desired number of rotations per minute (rpm) to cause each of the vibration motors to vibrate. In this way first lens 508 and second lens 510 may vibrate and cause dust and/or other contaminants to fall off a surface of the first lens 508 and second lens 510. In some examples, first component 506 and/or second component 504 may be supported by spring suspensions. Such spring suspensions may be may help to transfer vibrations of first vibration motor 902 and second vibration motor 904 to first lens 508 and second lens 510 respectively. In some examples, first vibration motor 902 and second vibration motor 904 may each include a plurality of vibrations motors physically coupled to first component 506 and second component 504 respectively. In some examples, the fifth embodiment including vibratory motors may be used if the docking system is in a vacuum environment and a gas flow is not available. In further examples, fifth embodiment 900 may be included in combination with any one or more of the first through fourth embodiments as described above. For examples, lenses may be automatically cleaned by vibrations generated by the vibration motors and by a gas stream directed through a nozzle. Alternatively, one of the lenses may be cleaned by vibrations and the other of the lenses may be cleaned by the gas stream.

First vibration motor 902 and second vibration motor may each be communicatively coupled to controller 806. Controller 806 may include instructions to activate and deactivate first vibration motor 902 and second vibration motor 904. Additionally, controller 806 may control a power and/or frequency of the vibrations generated by first vibration motor 902 and second vibration motor 904.

Turning now to FIG. 10, a flowchart of an example of a method 1000 for operating an automatic lens cleaning system is shown. The automatic lens cleaning system may be similar to one or more of fourth embodiment 800 shown in FIG. 8 or fifth embodiment 900 shown in FIG. 9. The automatic lens cleaning system may be incorporated into an imaging system including an imaging device and a reversibly coupled table, such as the imaging system 100 of FIGS. 1-2, the MRI apparatus of FIG. 3, and/or the MRI apparatus of FIG. 4. Method 1000 may be at least partially executed by instructions stored on non-volatile memory of a controller, such as controller 806 of FIGS. 8-9, table controller 108, and/or a device controller 104 as described above with respect to FIGS. 1-2, and/or a controller 25 of the MRI apparatus as shown in FIG. 3.

At 1002, method 1000 includes positioning a table for docking at an imaging device. The table may be a reversibly coupled table, such as reversibly coupled table 106 of FIGS. 1 and 2 or reversibly coupled table 404 of FIG. 4. Further, the table and imaging device may each include components of a docking system such as docking system 502 of FIGS. 5-9. Herein, the table and the imaging device may also encompass other components which include a docking system. Positioning the table for docking at the imaging system may include positing the table relative to the imaging system such that a lens of a docking device of the reversibly coupled table is positioned opposite a lens of a dock of the imaging device, such a docking device 408 and dock 406 of FIG. 4. Positioning the table for docking at the imaging device may include positioning the reversibly coupled table relative to the imaging device as shown in FIG. 4.

At 1004, method 1000 determines if the table docking is beginning. Docking may include automatically coupling the reversibly coupled table to the imaging device such that electrical and optical connections between the imaging device and the reversibly coupled table are aligned and then engaged. Docking may be initiated by the controller based on input from sensors and/or actuators of the imaging system. For example, a proximity sensor positioned on the imaging device and/or the reversibly coupled table may determine that the reversibly coupled table is close enough and in a proper orientation relative to the imaging device begin docking. Additionally or alternatively, a mechanical actuator, such as a switch may be activated when the docking device comes in close enough proximity to the dock.

If method 1000 determines that the table is not docking (NO), method 1000 continues to 1006 and determines if non-docking cleaning is requested. Non-docking cleaning may be cleaning that is activated by events other than the table docking with the imaging device. In one example, non-docking cleaning may be requested by the controller in response to determining that greater than a threshold amount of time has passed since the automatic lens cleaning system was last activated. In this way, excessive buildup of dust and other contaminants on a surface of the lenses may be avoided if the table is not often docked to the imaging device. As another example, non-docking cleaning may be requested by a user request through a user interface communicatively coupled to the controller. For example, a user may observe a contaminant producing event in proximity to the imaging device and/or table and may wish to preemptively clean a surface of the lenses. In this way, the lenses may be cleaned at times in addition to when docking occurs without demanding a presence of a specialized service technician.

If method 1000 determines that non-docking cleaning is not requested (NO), method 1000 continues to 1008 and includes waiting for table docking. During waiting for table docking, the controllers may be waiting for input that indicates the table is docking. The automatic lens cleaning system may not be activated while waiting for table docking. Method 1000 then returns to 1004 and again determines if the table docking is beginning.

If at 1004, method 1000 determines that the table is docking (YES) or at 1006, method 1000 determines that a non-docking cleaning is requested (YES), method 1000 continues to 1010 and includes activating the lens cleaning system. Activating the automatic lens cleaning system may include controlling an alternate gas source, such as a compressed gas cylinder or gas compressor to provide a flow gas to a nozzle. For example, activating the automatic lens cleaning system may include energizing a gas compressor and/or opening a valve positioned in a passage fluidly connecting the compressed gas cylinder to the nozzle. Additionally or alternatively, activating the automatic lens cleaning system may include energizing one or more vibration motors (e.g., first vibration motor 902 and second vibration motor 904 of FIG. 8) physically coupled to the table and/or the imaging device. Further, in examples where the system additionally includes an embodiment with bellows, such as the first embodiment, second embodiment, or third embodiments of the automatic lens cleaning system as show in FIGS. 3-7, activation may occur automatically in response to the table beginning to dock to the imaging device, driven by mechanical compression of bellows between the imaging device and the table.

Method 1000 then continues to 1012 and determines if table docking or the non-docking cleaning request is finished. Table docking may be finished with the imaging device is both electrically and communicatively coupled to the table. As one example, table docking may be finished when the lens of the imaging system and the lens of the table are at the fixed communication distance. A non-docking cleaning request may be finished after a determined period of time. The period of time may be given by instructions included in the controller and may be increased proportionally to an amount of time since the automatic lens cleaning system was last activated. As an alternate embodiment, the period of time may be input by a user interacting with the user interface. If method 1000 determines that the table docking or the non-docking request is not finished (NO), method 1000 continues to 1014 and includes maintaining active lens cleaning. For example, vibration motors and/or compressors may remain energized or valves as described above may remain open. Method 1000 then returns 1012 and again determines if mechanical docking or the non-docking cleaning request are finished.

If at 1012, method 1000 determines that table docking or non-docking cleaning request is finished (YES), method 1000 continues to 1016 and includes deactivating the automatic lens cleaning system. Deactivating the automatic lens cleaning system may include de-energizing the gas compressor or vibration motor and/or closing the valve described above. Additionally or alternatively, in examples where the automatic lens cleaning system is one of the first through third embodiments, the deactivating may occur automatically when the table is coupled to imaging device and all gas has been forced out of the bellows. Method 1000 ends.

The technical effect of method 1000 is to automatically clean exposed lenses of a communication interface of an imaging system including an imaging device and a reversibly coupled table. In this way, a clean and reliable communication interface between the imaging device and reversibly couple table may be maintained without attention from a user or a specialized technician. The automatic lens cleaning system may be mechanical and/or actuated by a controller and may include multiple embodiments. The multiple embodiments including both gas flow and vibratory cleaning. In this way, the system may be flexible and adapt to the different demands of different docking systems positioned in different environments.

The disclosure also provides support for a system, comprising: an imaging device, a reversibly coupled table, configured to reversibly couple to the imaging device, a communication interface comprising a first lens of the imaging device and a second lens of the reversibly coupled table, and an automatic lens cleaning assembly comprising a bellows positioned at a coupling interface between the imaging device and the reversibly coupled table and at least one nozzle fluidly connected the bellows, where the at least one nozzle is configured to direct a flow of gas towards at least one of the first lens or the second lens. In a first example of the system, the system is a magnetic resonance imaging apparatus. In a second example of the system, optionally including the first example, the flow of gas is directed downward with respect to gravity towards at least one of the first lens or the second lens. In a third example of the system, optionally including one or both of the first and second examples, the at least one nozzle is physically coupled to an outer surface of the imaging device or the reversibly coupled table and is configured to direct the flow of gas to the first lens and the second lens. In a fourth example of the system, optionally including one or more or each of the first through third examples, the at least one nozzle is embedded in the imaging device or the reversibly coupled table. In a fifth example of the system, optionally including one or more or each of the first through fourth examples, the automatic lens cleaning assembly further comprises a first embedded nozzle embedded in the reversibly coupled table and a second embedded nozzle embedded in the imaging device. In a sixth example of the system, optionally including one or more or each of the first through fifth examples, the first embedded nozzle is fluidly coupled to the bellows and the second embedded nozzle is fluidly coupled to the first embedded nozzle.

The disclosure also provides support for a docking system, comprising: a first component including a first lens, a second component including a second lens, wherein the first lens and second lens are configured to communicatively couple the first component to the second component when the docking system is in a coupled state, an automatic lens cleaning system configured to automatically remove contaminants from a surface of the first lens and second lens in response to the docking system transitioning from a decoupled state to the coupled state by gas flow and/or vibrations. In a first example of the system, the first lens and second lens are fiber optic lenses configured to communicatively couple the first component to the second component via a fiber optic cable. In a second example of the system, optionally including the first example, the automatic lens cleaning system includes a vibration motor physically coupled to the first component or the second component. In a third example of the system, optionally including one or both of the first and second examples, the automatic lens cleaning system includes a gas source fluidly coupled to a nozzle, wherein the gas source is one or more of a bellows or an alternate gas source. In a fourth example of the system, optionally including one or more or each of the first through third examples, the alternate gas source is one or more of a gas compressor, a compressed gas cylinder, or a patient blower. In a fifth example of the system, optionally including one or more or each of the first through fourth examples, the system further comprises: a controller including instructions stored on non-volatile memory, the instructions executable to: activate the automatic lens cleaning system in response to the first component beginning to dock with the second component. In a sixth example of the system, optionally including one or more or each of the first through fifth examples, the instructions are further executable to deactivate the automatic lens cleaning system in response to docking of the first component with the second component being finished.

The disclosure also provides support for a method, comprising: determining if a reversibly coupled table is beginning to dock to an imaging device, in response to the reversibly coupled table beginning to dock to the imaging device, activating an automatic lens cleaning system, wherein the automatic lens cleaning system removes contaminants from a lens of the reversibly coupled table and from a lens of the imaging device using gas flow and/or vibrations, and in response to the reversibly coupled table not beginning to dock, waiting for table docking to begin. In a first example of the method, the automatic lens cleaning system includes a bellows and activating includes compressing the bellows between the reversibly coupled table and the imaging device. In a second example of the method, optionally including the first example, the automatic lens cleaning system includes an alternate gas source and activating the automatic lens cleaning system includes energizing a compressor and/or opening a valve. In a third example of the method, optionally including one or both of the first and second examples, the automatic lens cleaning system includes a vibration motor and activating the automatic lens cleaning system includes energizing the vibration motor. In a fourth example of the method, optionally including one or more or each of the first through third examples, the method further comprises: deactivating the automatic lens cleaning system in response to docking being finished, wherein docking is finished when a lens of the reversibly coupled table is at a fixed communication distance from a lens of the imaging device. In a fifth example of the method, optionally including one or more or each of the first through fourth examples, the method further comprises: activating the automatic lens cleaning system in response to determining non-docking cleaning is requested.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

FIGS. 4-9 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. FIG. 4 is shown approximately to scale, however, other dimensions may be used if desired.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
an imaging device;
a reversibly coupled table, configured to reversibly couple to the imaging device;
a communication interface comprising a first lens of the imaging device and a second lens of the reversibly coupled table; and
an automatic lens cleaning assembly comprising a bellows positioned at a coupling interface between the imaging device and the reversibly coupled table and at least one nozzle fluidly connected the bellows, where the at least one nozzle is configured to direct a flow of gas towards at least one of the first lens or the second lens, wherein the flow of gas is caused by compression of the bellows between the imaging device and the reversibly coupled table.

2. The system of claim 1, wherein the system is a magnetic resonance imaging apparatus.

3. The system of claim 1, wherein the flow of gas is directed downward with respect to gravity towards at least one of the first lens or the second lens.

4. The system of claim 1, wherein the at least one nozzle is physically coupled to an outer surface of the imaging device or the reversibly coupled table and is configured to direct the flow of gas to the first lens and the second lens.

5. The system of claim 1, wherein the at least one nozzle is embedded in the imaging device or the reversibly coupled table.

6. The system of claim 1, wherein the automatic lens cleaning assembly further comprises a first embedded nozzle embedded in the reversibly coupled table and a second embedded nozzle embedded in the imaging device.

7. The system of claim 6, wherein the first embedded nozzle is fluidly coupled to the bellows and the second embedded nozzle is fluidly coupled to the first embedded nozzle.

8. A docking system, comprising:
a first component including a first lens;
a second component including a second lens, wherein the first lens and second lens are configured to communicatively couple the first component to the second component when the docking system is in a coupled state;
an automatic lens cleaning system configured to automatically remove contaminants from a surface of the first lens and second lens in response to the docking system transitioning from a decoupled state to the coupled state by gas flow and/or vibrations; and
a controller including instructions stored on non-volatile memory, the instructions executable to:

17 activate the automatic lens cleaning system in response to the first component beginning to dock with the second component.

9. The docking system of claim 8, wherein the first lens and second lens are fiber optic lenses configured to communicatively couple the first component to the second component via a fiber optic cable.

10. The docking system of claim 8, wherein the automatic lens cleaning system includes a vibration motor physically coupled to the first component or the second component.

11. The docking system of claim 8, wherein the instructions are further executable to deactivate the automatic lens cleaning system in response to docking of the first component with the second component being finished.

12. The docking system of claim 8, wherein the automatic lens cleaning system includes a gas source fluidly coupled to a nozzle, wherein the gas source is one or more of a bellows or an alternate gas source.

13. The docking system of claim 12, wherein the alternate gas source is one or more of a gas compressor, a compressed gas cylinder, or a patient blower.

14. A method, comprising:
determining if a reversibly coupled table is beginning to dock to an imaging device;
in response to the reversibly coupled table beginning to dock to the imaging device, activating an automatic lens cleaning system, wherein the automatic lens cleaning system removes contaminants from a lens of the reversibly coupled table and from a lens of the imaging device using gas flow and/or vibrations; and
in response to the reversibly coupled table not beginning to dock, waiting for table docking to begin.

15. The method of claim 14, wherein the automatic lens cleaning system includes a bellows and activating includes compressing the bellows between the reversibly coupled table and the imaging device.

16. The method of claim 14, wherein the automatic lens cleaning system includes an alternate gas source and activating the automatic lens cleaning system includes energizing a compressor and/or opening a valve.

17. The method of claim 14, wherein the automatic lens cleaning system includes a vibration motor and activating the automatic lens cleaning system includes energizing the vibration motor.

18. The method of claim 14, further comprising deactivating the automatic lens cleaning system in response to docking being finished, wherein docking is finished when a lens of the reversibly coupled table is at a fixed communication distance from a lens of the imaging device.

19. The method of claim 14, further comprising activating the automatic lens cleaning system in response to determining non-docking cleaning is requested.

* * * * *